United States Patent
Suaning (10) Patent No.: US 7,818,876 B2
(45) Date of Patent: Oct. 26, 2010

(54) METHOD FOR FABRICATION OF HERMETIC ELECTRICAL CONDUCTOR FEEDTHROUGHS

(76) Inventor: Gregg Jorgen Suaning, 115 Taylor Road, Lisarow, NSW (AU) 2250

( * ) Notice: Subject to any disclaimer, the term of this patent is extended or adjusted under 35 U.S.C. 154(b) by 472 days.

(21) Appl. No.: 11/786,896

(22) Filed: Apr. 12, 2007

(65) Prior Publication Data

US 2007/0277374 A1 Dec. 6, 2007

Related U.S. Application Data

(60) Provisional application No. 60/794,590, filed on Apr. 25, 2006.

(51) Int. Cl.
*H01R 43/00* (2006.01)
(52) U.S. Cl. ............... 29/825; 29/830; 29/832; 29/846; 29/852
(58) Field of Classification Search .......... 29/825, 29/830, 832, 846, 852
See application file for complete search history.

(56) References Cited

U.S. PATENT DOCUMENTS

| | | | | |
|---|---|---|---|---|
| 3,522,575 A | * | 8/1970 | Johnson et al. | ............. 439/281 |
| 4,050,956 A | | 9/1977 | De Bruin | |
| 6,458,157 B1 | | 10/2002 | Suaning | |
| 7,210,966 B2 | * | 5/2007 | Taylor et al. | ........... 439/620.09 |
| 7,396,265 B2 | * | 7/2008 | Darley et al. | ................ 439/885 |
| 2003/0213604 A1 | * | 11/2003 | Stevenson et al. | ......... 174/35 R |
| 2007/0122932 A1 | * | 5/2007 | Kodas et al. | .................. 438/57 |
| 2008/0208289 A1 | * | 8/2008 | Darley et al. | .................. 607/57 |
| 2008/0209723 A1 | * | 9/2008 | Darley et al. | .................. 29/854 |

OTHER PUBLICATIONS

Allen, et. al "Solid state metal-ceramic bonding of platinum to alumina" *Journal of Materials Science* 18 (1983) 2835-2843.
Merrill, et al. "Electrical stimulation of excitable tissue: design of efficacious and safe protocols" *Journal of Neuroscience Methods* 141 (2005) 171-198.

* cited by examiner

*Primary Examiner*—C. J Arbes
(74) *Attorney, Agent, or Firm*—Ballard Spahr LLP (57) ABSTRACT

A method is disclosed for the fabrication of feedthrough devices that can transmit a single or plurality of electrical signal(s) to or from within a leak-tight (hermetic) chamber from or to the outside of said leak-tight (hermetic) chamber. The invention allows materials known to be well-tolerated within the human body such as alumina-oxide ceramic and platinum to be used as raw materials in the fabrication of body-compatible, single or multi-channel leak-tight (hermetic) feedthroughs.

16 Claims, 4 Drawing Sheets

METHOD FOR FABRICATION OF HERMETIC ELECTRICAL CONDUCTOR FEEDTHROUGHS

CROSS REFERENCE TO DISCLOSURE DOCUMENT

This application is based upon Provisional Application for Patent 60/794,590 filed 25 Apr. 2006. Priority is claimed thereto.

FIELD OF THE INVENTION

The present invention is directed generally to approaches to the passage of one or more electrical signals across a leak-tight (hermetic) barrier. More specifically, the present invention is directed to the use of methods of enclosing electronics within a leak-tight (hermetic) chamber in such a way as to facilitate the passage, in either direction, of electrical signal or signals from within said leak-tight (hermetic) chamber to outside said chamber, without significantly compromising the effectiveness of the leak-tight (hermetic) chamber through the introduction of leaks.

BACKGROUND OF THE INVENTION

It is often the case where an electronic circuit comprised of semiconductor (and perhaps other) components must be sealed within a leak-tight chamber so as to protect it from corrosive or otherwise damaging environmental conditions. As an illustrative example, consider a medical implant that requires that electronics must function inside the body for many years. Unless protected, the sodium and other ions that are present within the body would rapidly begin to corrode said electronics, severely compromising the device's longevity. The cardiac pacemaker, for example, is a device which must function under such conditions. As such, the cardiac pacemaker must be sealed within a chamber that is leak-tight (hermetic). While most of the hermetic chamber can be manufactured from a metallic material and thus also serve to complete a cardiac stimulation circuit (the so-called hot-can approach), the electrode placed within or near the heart must be insulated from said hermetic chamber without compromising the hermetic integrity of the pacemaker body containing the electronics. In this example, one electrical conductor must pass through the wall of the hermetic chamber so as to allow for the delivery of therapeutic electrical stimuli via an electrode connected to said electrical conductor on the outside of the hermetic chamber. In most cases, said electrical conductor is encased within a glass, ceramic or other appropriate insulator thereby forming a hermetic feedthrough. Said hermetic feedthrough is then attached to the remainder of the pacemaker body by way of brazing, welding, or other appropriate means. The invention described herein pertains mainly to the fabrication of leak-tight (hermetic) feedthrough assemblies with one or more isolated electrical conductors therein.

In the case of medical implants such as the cardiac pacemaker, the cochlear implant, and other therapeutic devices that must communicate electrical signals originating from, or destined for electrical circuitry within a hermetic chamber, a conductor or multiple conductors are typically oriented within the hermetic feedthrough perpendicular to the wall of said hermetic chamber so as to facilitate the passage of signals. Inherent to this design, in medical or corrosive applications in particular, said conductor or conductors and the insulating material within which they are placed must be comprised of non-reactive, non-corrosive, so-called inert materials such as platinum and ceramic. For example, platinum wire or wires are placed within a ceramic insulator prior to sintering of said ceramic. During the sintering process, the expansion and contraction properties of the two materials are such that leaks along the side of each conductor may occur. In this example, during the sintering process, the platinum expands relatively more than the ceramic thereby leaving behind a hole of greater diameter than the diameter of the conductor intended to fill it. The result is that after the sintering process and subsequent cooling, leaks can be identified. As the quantity of conductors increase, so too does the probability of compromising the hermetic properties of the hermetic feedthrough.

In 1977, de Bruin and colleagues (U.S. Pat. No. 4,050,956) patented a technique for the purpose of joining two or more ceramic bodies. The present invention, while using the natural phenomenon of bonding described within de Bruin's patent, pertains more specifically to the utilization of the aforementioned natural phenomenon of bonding rather than the bonding itself. A principal advantage of the present invention is, by way of the planar and layered structuring, the ability to promote the formation of bonding (mechanical, chemical or otherwise) between the insulator and the metallic conductor thereby improving the hermeticity. This is in contrast to existing methods wherein wires are individually cast into an insulating material in order to form an assembly. As such, no mechanism exists to promote bonding. Indeed in such cases the tendency towards the aforementioned formation of bonding is reduced or eliminated, with the hermeticity achieved only by way of tight dimensions.

Despite the differential expansion and contraction properties of platinum and ceramic, Researchers Allen and Borbidge published work in 1983 that identified that, through the application of compressive force during the sintering process, an improved bond strength can be created between platinum and ceramic (as well as other material combinations). The aforementioned fabrication method with conductors oriented perpendicular to the wall of the hermetic chamber does not lend itself to the application of pressure unless said pressure can be applied in all directions at the same time. While isostatic pressing during sintering is indeed possible, this approach substantially complicates the fabrication procedure thus highlighting one of the advantages of the present invention.

SUMMARY OF THE INVENTION

Accordingly, in one embodiment, the present invention proposes that a stacked assembly be constructed comprising a substrate material of previously sintered and densified ceramic ($Al_2O_3$ for example) covered with a thin layer of slurry comprised of ceramic particulate (for example, of the same chemical composition as the substrate) and, if necessary, an appropriate binder, followed by a pre-patterned layer of foil (e.g. Pt), then by a second layer of slurry similar to the first, and topped with a second previously sintered and densified ceramic (for example, of the same material composition as the substrate). Said assembly is then placed in a heated environment wherein forces longitudinal to the stacked structure can be applied, and brought to a temperature where recrystallization (sintering) of the slurry occurs. The sintering process binds the slurry to the previously sintered and densified ceramic. Elevated temperature in conjunction with the longitudinal forces (applied or intrinsic) promotes bonding of the slurry to the pre-patterned layer of foil (e.g. Pt). Following cooling, the assembly comprises an upper surface and a lower surface. One or more perpendicular excavations in pre-determined locations are made on the upper surface to a depth sufficient to expose the surface or some part of the foil (e.g. Pt). Corresponding, but not necessarily co-axial excavations can be made on the lower surface. An appropriate material may be filled into said excavations. This may be any appropriate conductor including platinum, and may be applied by any appropriate method including electroplating.

An alternative embodiment of the invention describes that the foregoing ceramic components of the assembly be made in whole or in part from unsintered ceramic slurry or particulate. In this embodiment, an organic binder may be used in order to promote light adhesion between ceramic particles so that a structure may be formed and maintained prior to sintering.

A preferred embodiment of the invention describes that the pre-patterned layer of foil be shaped such that all areas of said foil are electrically connected so as to facilitate electroplating with one electrical connection to said pre-patterned layer of foil. In this embodiment, an appropriate means of isolating each individual conductor after electroplating would be incorporated, for example, by way of removing a portion or portions of the foil that introduce short circuits between conductors, or by severing short circuits through the passage of current sufficient to permanently break the continuity.

A further alternative embodiment of the invention describes a means for incorporation of an electrode array (or part thereof) within said pre-patterned layer of foil with none, all, or part of said electrode array patterned after sintering. Through this embodiment, interconnections need not be made to the electrode array as these interconnections are incorporated within the patterning.

Another alternative embodiment of the invention describes a means for multiple, interleaved layers of foil and insulator so as to allow for an increase in the quantity of electrical conductors within the device.

An alternative embodiment of the invention describes a means for forming a barrier wherein the path of electrical conduction may be directed in angles other than coaxial, including that conductors may exit the side of the structure which connect the upper and lower surfaces.

Another alternative embodiment of the invention describes a means of incorporating lead wires and other structures such as electrode arrays into the conductive layer or layers such that the feedtrough assembly forms a homogeneous structure with said other structures such as electrode arrays.

Accordingly, it is a basic object of the invention to disclose a method for fabricating devices that can transmit a single or plurality of electrical signal(s) to or from one side of a leak-tight (hermetic) barrier from or to the other side of said leak-tight (hermetic) barrier. The invention allows materials known to be well-tolerated within the human body such as alumina-oxide ceramic and platinum to be used as raw materials in the fabrication of body-compatible, single or multi-channel leak-tight (hermetic) feedthroughs.

It is another object of the invention to disclose a fabrication means through which a layered structure is fabricated in a planar fashion so as to allow for longitudinal forces to be applied as an aid to bonding metallic conductors to the insulator during the sintering process.

Another object of the invention is to disclose how multiple layers of interleaved conductive and insulative materials can be formed so as to facilitate an increase in electrical conductor quantities.

It is another object of the invention to disclose how individual conductors may enter on one of the upper or lower surfaces of the barrier, and exit via the side of the barrier (thereby forming an approximate right angle path of electrical conduction).

DESCRIPTION OF PRIOR ART

Electrical feedthroughs convey electrical signals from one side of a barrier to another. In an illustrative example in simple form, consider a metal pipe wherein a fluid flows. It is of interest to remotely monitor the temperature of the fluid inside the pipe yet in so doing no leaks can be made to occur. The temperature measurement can be achieved by way of a temperature detector such as a thermocouple comprised of two wires (the first and second wires). Given that the pipe is metallic and thus itself a conductor, the first thermocouple wire may be attached to the inside wall of the pipe. External (remote) monitoring equipment outside the pipe is thus connected to the outer wall of the pipe in order to connect to the signals conveyed on the first thermocouple wire. The second thermocouple wire must exit the pipe without forming an electrical connection to said pipe and thus shorting the thermocouple. Further, as the second wire exits the pipe, it must not allow the contents of the pipe to leak out. It is the passage of this second electrical conductor that requires a hermetic feedthrough. In this simple, illustrative example, a small hole is placed within the wall of the pipe, the wire is subsequently passed through the hole and connected to the external (remote) monitoring equipment thereby completing the circuit with the first thermocouple wire. The hole in the pipe is back-filled with an electrical insulator such as epoxy so as to seal the leak. Provided that the pressure within the pipe is not sufficiently large as to dislodge the epoxy, or, the material conveyed within the pipe or the environment surrounding the pipe does not corrode the material that comprises the second wire or otherwise damage the epoxy, the design of this example feedthrough is sufficient for its intended purpose.

In reference to the foregoing illustrative example, a hermetic feedthrough intended for implantation within a living body would likely be insufficient if constructed as described above. For instance, the corrosive nature of body fluids would substantially limit the materials that could be used as an electrical conductor. Moreover, epoxy may be toxic to body tissue or otherwise be damaged, over time, by the chemical composition of the fluids in which it is immersed.

Of particular concern in body implantable electronics is corrosion of active electronics within said implant. If the level of hermeticity achieved by the hermetic feedthrough is insufficient to prevent passage of water and other molecules into the implant, it may lead to a corrosive environment being formed within the implant which, eventually, can cause device failure through degradation of the electronics.

As such, a number of limitations must be applied to body-implantable hermetic feedthroughs. First, the material composition of the hermetic feedthrough must be compatible with biological tissue. Second, the longevity of the hermetic feedthrough must be such that it exceeds the intended lifetime of the implant, which is often the lifetime of the implant recipient. Third, the level of hermeticity of the feedthrough must be such that, over the lifetime of the implant, the moisture content within the implant must not be allowed to reach a level at which condensation (and therefore corrosion) may occur.

Given these limitations, very few options are afforded to designers of long-term medical implants containing active electronics and so the state of the art of hermetic feedthroughs remains rather limited.

With regard to materials, only a few have a demonstrated history of biological compatibility. A small subset of these can be used as electrical conductors within the body (Merrill et al, 2005). Among the most prevalent of these is platinum. For insulation, a similar story applies in terms of limitations in biological compatibility. Combine the limited list of materials with those which are capable of forming a long-term hermetic seal, designers are left with few options. For hermetic feedthroughs, the most commonly used hermetic feedthrough materials in pacemakers, cochlear implants, and other active implantable electronic devices are alumina-based ceramics and platinum.

Formation of feedthroughs comprised of these materials with low numbers of conductors (approximately 25 or less) is often achieved by casting platinum wires within a ceramic body and co-firing the assembly so as to achieve a single or multiple conductor feedthrough. During the heating process, however, the coefficients of linear thermal expansion are greater for Pt than they are for $Al_2O_3$. As such, the tendency is for Pt to expand and contract to a greater extent than the $Al_2O_3$ thereby leaving behind a larger hole than the Pt can occupy upon cooling. This potentially compromises the hermetic integrity of the assembly.

Beyond a few tens of conductors within the feedthrough, the reliability of this method is compromised to such an extent that it is no longer practical and alternatives —such as those disclosed in the present invention—are necessary when approaching the design of, for example, a visual prosthesis for the blind such as that disclosed by the present inventor in U.S. Pat. No. 6,458,157.

PATENT REFERENCES de Bruin et al. U.S. Pat. No. 4,050,956
Suaning U.S. Pat. No. 6,458,157

NON-PATENT REFERENCES

Allen, R. V., Borbidge, W. E. (1983) J. Mater. Sci. 18:2835-43 39.
D. Merrill, M. Bikson, and J. Jefferys, (2005) "Electrical stimulation of excitable tissue: design of efficacious and safe protocols, J Neurosci Meth, vol. 141, pp. 171198

BRIEF DESCRIPTION OF THE DRAWINGS

The invention will now be described in more detail, by way of example only, with reference to the accompanying drawings, in which.

While the patent invention shall now be described with reference to the preferred embodiments shown in the drawings, it should be understood that the intention is not to limit the invention only to the particular embodiments shown but rather to cover all alterations, modifications and equivalent arrangements possible within the scope of appended claims.

Throughout this discussion which follows, it should be understood that the terms "implant", "neural prosthesis", and other terms of this nature are used in the functional sense and not exclusively with reference to specific medical devices, mechanical or electrical equivalents, components, or arrangements. Moreover, "feedthrough", or "hermetic feedthrough" are used interchangeably and includes one electrical conductor or equivalent, or plurality of electrical conductors. Furthermore, "$Al_2O_3$", "titanium", "platinum" and other elements or materials within the discussion should be understood to include alloys or doped variations thereof.

DESCRIPTION OF THE PREFERRED EMBODIMENT

An important factor that determines the longevity of an electronic circuit is its ability to withstand damage from corrosion. Ideally, said corrosion is prevented by sealing the electronics within a chamber that is either held in vacuum, or filled with an inert gas. This chamber is termed hermetic when sealed. However, even with this precaution, diffusion of ions over the lifetime of the electronics can lead to sufficient quantities of corrosive matter such that damage to the electronics can occur. This situation is of critical importance in the manufacturing of implantable medical devices that include electronics cochlear implants, cardiac pacemakers, and other devices containing electronics that are implanted within body.

The present invention describes a methodology for an improved hermetic chamber that also allows for the transmission of single or a plurality of electrical signals through said hermetic chamber. Said hermetic chamber is comprised of an electrical insulator (ceramic, for example) and an electrical conductor, or plurality thereof.

Said electrical conductor is formed, either previously or during the fabrication process, by way of laser machining and subsequent removal of excess material.

In the design of a metallic foil pattern containing a plurality of electrical conductors, it is readily possible to electrically connect all areas of said metallic foil to a common point that can subsequently be removed (e.g. through mechanical removal, the passage of electrical current, etc.) thereby allowing one connection to be made to facilitate electroplating.

For body-implantable devices, there are limited materials that may be used owing to their favorable interaction with biological tissue. However, while an illustrative example described herein pertains specifically to a body-implantable device, the methodology need not be limited to the materials or applications described therein and can apply to any combination of electrical conductor and insulator in which advantage is gained towards fabrication efficiency and/or hermeticity improvement.

$Al_2O_3$ ceramic (and some alloys thereof), Ti (and some alloys thereof) and Pt (and some alloys thereof) are commonly used in implantable medical devices owing to their longevity and compatibility with biological tissue. As such, these materials shall be used in a non-limiting illustrative example of the present invention.

Figure 1:
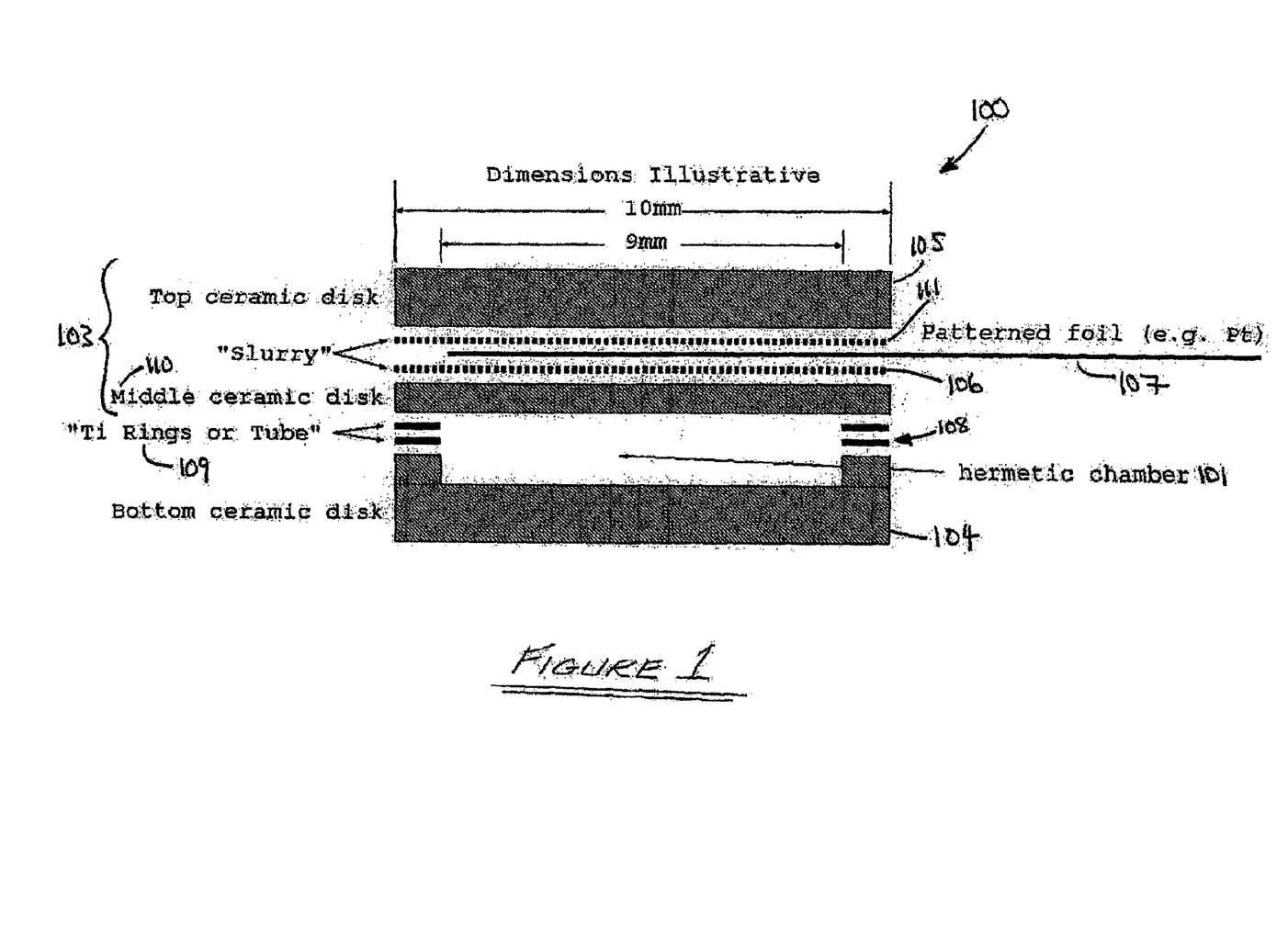
FIG. 1 an illustrative example of the component assembly comprising the fabrication process.

FIG. 1 illustrates one embodiment of the invention. In this Figure, a hermetic chamber 101 comprising one or more electrical conductors in a medical implant assembly 100 is shown in cross-sectional view. The assembly may be formed in two parts, an upper part 103 a lower part 104 with the former 103 comprising the top ceramic disk 105, slurry 106 and 111, patterned foil 107, and middle ceramic disk 110, and the latter 104 comprising the bottom ceramic disk. The interface 108 between the upper part 103 and the lower part 104 may be formed with titanium or other appropriate material 109 that forms a bond with the ceramic and can be welded (e.g. with a laser) in a relatively low-temperature operation that electronics may withstand in order to complete and seal the assembly.

In reference to the Figures and the description relating thereto, the term disk need not specifically apply to circular shapes as the present invention can apply to any appropriate shape.

Figure 3:
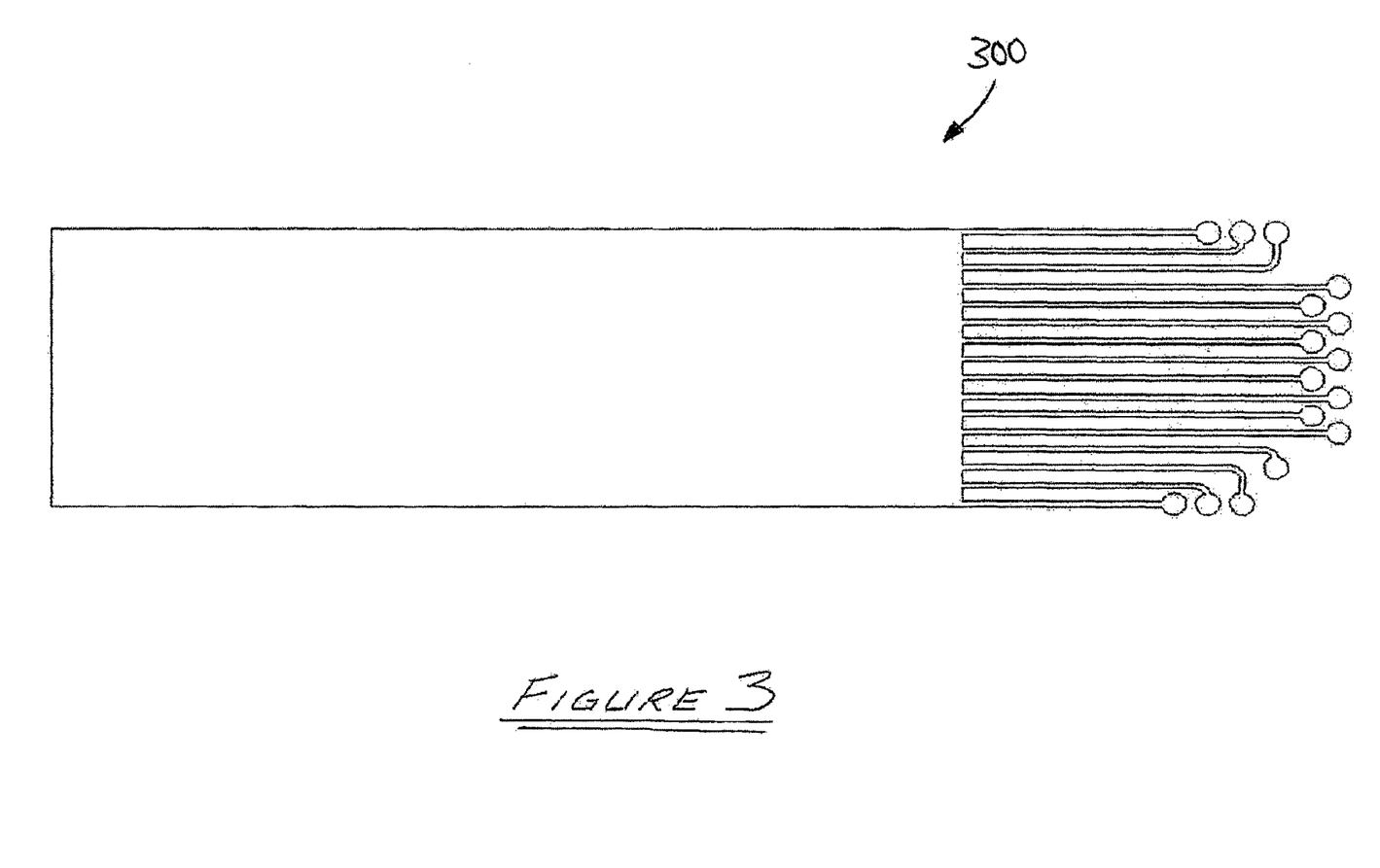
FIG. 3 top view of part of a patterned metallic foil that forms whole or part of the electrode array. The electrodes (not shown) would appear on the left of the drawing (to the left of the vertical line). These can be formed either before or after the assembly described herein.

Further referencing FIG. 1, the assembly of the upper part 103 may progress as follows: the Middle Ceramic Disk 110 is comprised of an electrical insulator (e.g. $Al_2O_3$ ceramic) upon which is placed a slurry 106 comprised, for example, of a suspension of $Al_2O_3$ ceramic particles in a liquid. Above the slurry is placed a patterned metallic foil that serves as a conductor 107, or plurality of conductors. Said pattern may be a simple shape (e.g. a circle or square) in the case of a single electrical conductor, or a complex pattern such as that shown in FIG. 3 in the case of multiple electrical conductors. Said patterned metallic foil (e.g. Platinum) may or may not protrude from the assembly 100 such as shown at the right of FIG. 1. A second layer of slurry 111 is placed on top of the patterned metallic foil 107 followed by a Top Ceramic Disk electrical insulator 105 (e.g. $Al_2O_3$ ceramic). The assembly of the top part is heated by any appropriate means (e.g. furnace) to a temperature sufficient to cause recrystallization or sintering of the electrical insulator at a temperature below the melting point of the material but sufficient to propagate crystal formation between the slurry and the top ceramic disk and the slurry and the bottom ceramic disk. As described by Allen and Borbidge in their published work of 1983 application of pressure (e.g. 2 MPa) during the heating and subsequent cooling may aide in forming a stronger bond between the electrical insulator and the patterned metallic foil thereby improving the seal between these two materials. The inventor has observed sufficient bonding in the absence of applied pressure so the application of pressure is an option should the bond strength be a factor in a given design as opposed to simply the hermetic integrity of said bond.

The lower part assembly 104 (the Bottom Ceramic Disk) is comprised of an insulator (e.g. $Al_2O_3$ ceramic) that is densified by way of heating (sintering). By way of the geometry of the bottom ceramic disk, it may (as shown) possess a recess 101 that will eventually form the void within the assembly labelled hermetic chamber in the figure.

The next step in the non-limiting illustrative example of the assembly involves the bonding of Titanium Rings or Tube 109 to the top part 103 and bottom part 104. In the case of the use of rings, placement of titanium rings on each part (upper 103 and lower 104) in the locations shown in FIG. 1 and subsequent heating (with added pressure if necessary) forms a diffusion bond between the titanium and the ceramic. The two parts (upper 103 and lower 104) are abutted at the interface of the two titanium rings and, after any subsequent assembly procedures are complete, joined by way of applied heat, preferably in a localized area such as by way of heating with a laser so as to avoid damage to any electronics placed within the hermetic chamber formed by the joining of the upper 103 and lower 104 parts. Normally this would occur in a vacuum or dry, inert environment so as to avoid including oxygen and moisture within said hermetic chamber.

In an alternative embodiment of the invention, said titanium rings may be replaced with a single titanium tube such that the upper and lower parts may be joined together but subsequently separated by parting the titanium tube. Said separation facilitates assembly/insertion of electronics into the hermetic chamber. As above, the upper and lower parts are eventually joined by an appropriate bonding means.

Figure 2:
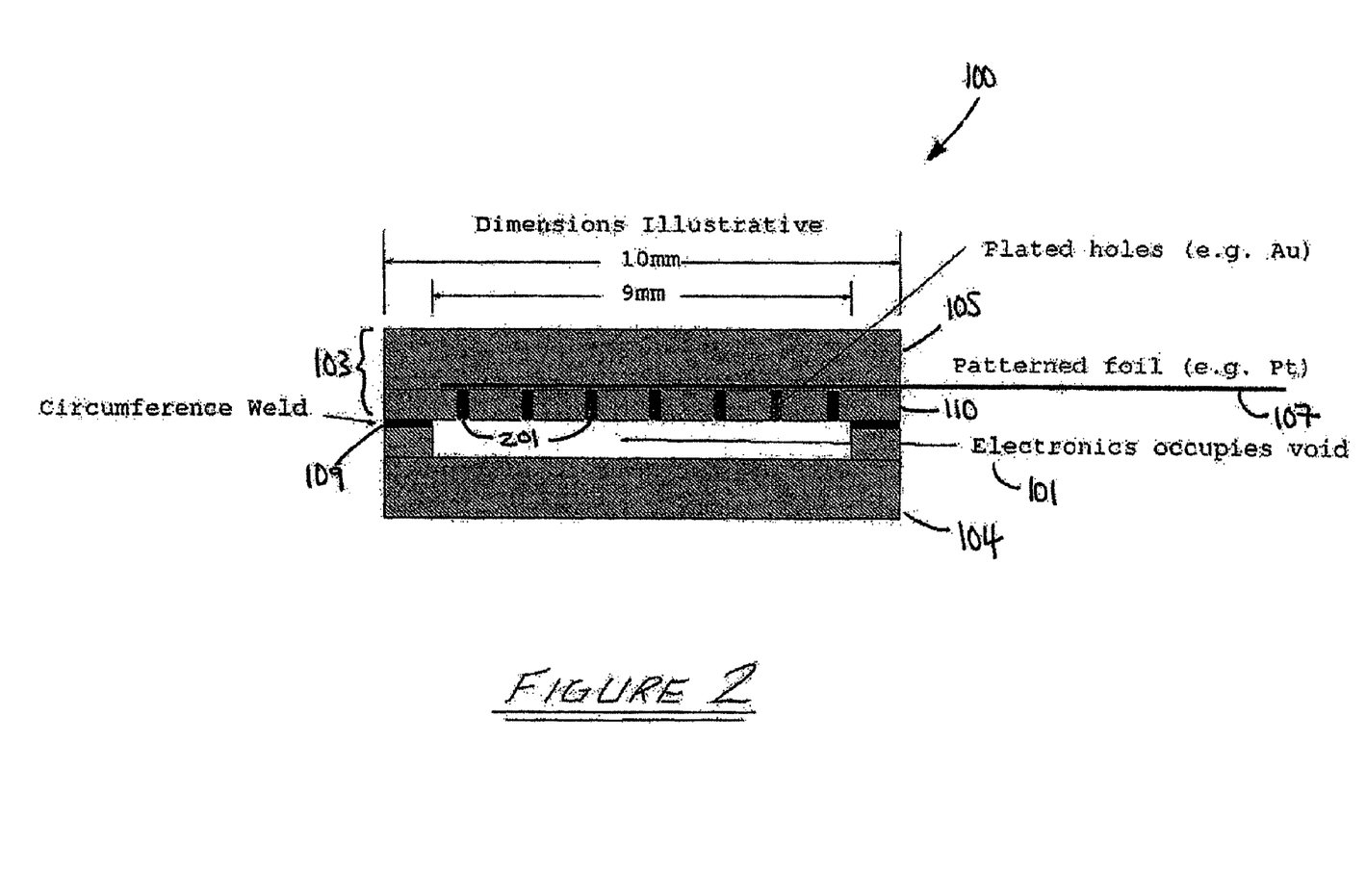
FIG. 2 an illustrative example of a device fabricated using the method described herein.

Prior to the joining of the upper part to the lower part, however, FIG. 2 illustrates a further step in the illustrative embodiment of the invention wherein the separated upper 103 and lower 104 parts are further processed thus: in the insulating material that was originally the Middle Ceramic Disk 110 of FIG. 1, holes 201 are formed (e.g. by drilling) down to, or partially or fully through the Patterned metallic foil 107; an electrical connection may be established to facilitate electroplating of the inside of each of said holes; the holes are electroplated with gold or other appropriate conductive material thereby producing means of connecting electrical signals to each of the conductors inside the hermetic chamber. Said connections may also be achieved by way of any other appropriate means as an alternative to electroplating. In the example of gold plating, each filled hole then serves as a point to bond wires or other electrical connections to the conductors. Upon completion of attachment of electronics to conductors in the patterned metallic foil, and completion of any other assembly requirements within the hermetic chamber, the top half 103 and bottom half 104 are (re-)assembled as described above thereby completing the hermetic assembly.

Figure 4:
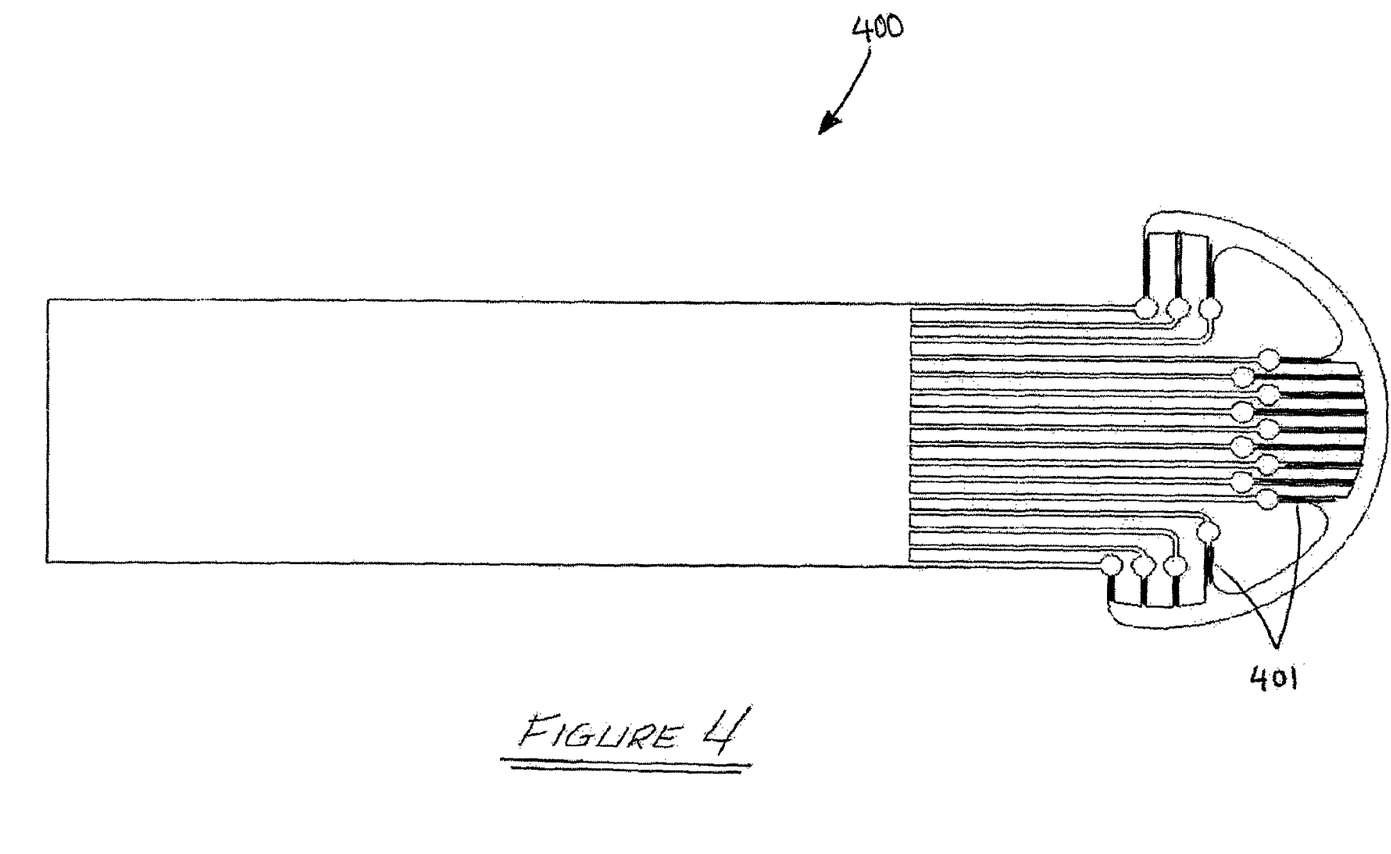
FIG. 4 as FIG. 3 with an additional patterned structure. If the horizontal tracks shown in the dashed section are made sufficiently more narrow than the solid tracks to their left, passage of current from left to right or right to left can cause the tracks shown in the dashed section to permanently break thereby isolating individual tracks from one another.

An optional addition to the patterned metallic foil 300 is shown in example form 400 in FIG. 4. As handling of the delicate foil structures is difficult, improved resistance to damage can be had through the addition of the pattern shown in, for example, bold lines 401 of FIG. 4. If the tracks shown in bold lines have a smaller cross-section than all other tracks, after the required handling and processing, an electrical current can be passed through the structure from left to right or right to left and will heat the thin tracks of the pattern shown in bold lines. If said current is sufficiently high in magnitude, these tracks will break and isolate the remaining tracks from one another (in the case of a partially patterned electrode, this occurs after the remainder of the electrode is fully patterned).

The principal advantage of this methodology is, by way of the planar and layered structuring, the ability to promote the formation of bonding (mechanical, chemical or otherwise) between the insulator 105, 110 and the metallic conductor 107 thereby improving the hermeticity. This is in contrast to existing methods wherein wires are individually cast into an insulating material in order to form an assembly in this way, no mechanism exists to promote bonding. Indeed in such cases the tendency towards the formation of the aforementioned formation of bonding is reduced or eliminated, with the hermeticity achieved only by way of tight dimensions.

Enhancements

While the present invention primarily pertains to implementations of neuroprostheses, advantage is realized by utilizing the same feedthrough methods in other areas of sensors or actuators susceptible to damage through exposure to corrosive fluids. For example, sensors within any chamber can have their signals conveyed by way of a feedthrough fabricated by way of the present invention. Similarly, power or data can be conveyed to a device that is otherwise inaccessible to wires or where sealing such wires by other means is impractical or ineffective.

Benefits of the Invention

Placement of any device in the presence of fluids exposes any component of said device susceptible to corrosion to the risk of damage that can ultimately lead to compromised device functionality. The present invention describes a method of sealing electronics within a chamber such that diffusion of corrosive fluids is prevented while at the same time allowing one or multiple electrical signals to pass through said chamber such that communication from inside to outside the chamber is made possible without the use of materials that are significantly harmful to biological tissue thereby making implementation in medical implants particularly advantageous. The invention provides improved means through which the number of individual electrical signals may pass can be increased, and, owing to the planar nature of the method, can be more readily manufactured over existing methods of feedthrough fabrication.

Other Embodiments

From the foregoing description, it will thus be evident that the present invention provides a method for fabricating leak-tight devices capable of transmitting a single or plurality of electrical signal(s) to or from one side to the other, for example, from within a leak-tight (hermetic) chamber from or to the outside of said leak-tight (hermetic) chamber. The invention makes possible the utilization of materials in its composition such as alumina-oxide ceramic and platinum that are known to be well-tolerated within living tissue. As various changes can be made in the above embodiments and operating methods without departing from the spirit or scope of the following claims, it is intended that all matter contained in the above description or shown in the accompanying drawings should be interpreted as illustrative and not in a limiting sense.

Variations or modifications to the design and construction of this invention, within the scope of the appended claims, may occur to those skilled in the art upon reviewing the disclosure herein. Such variations or modifications, if within the spirit of this invention, are intended to be encompassed within the scope of any claims to patent protection issuing upon this invention.

The invention claimed is:

1. A method for forming an hermetically sealed feedthrough through an insulating body of an hermetic chamber, the insulating body including a planar ceramic insulating wall, the method comprising:
   a) assembling a stacked structure including a plurality of planar layers, the plurality of layers comprising:
      the planar ceramic insulating wall defining a plane for the stacked structure;
      a planar conductor positioned parallel to the plane of the stacked structure, wherein in end use the planar conductor is in conductive communication with the hermetic chamber via at least one conductive channel through the planar ceramic insulating wall;
      a planar ceramic insulator positioned parallel to the plane of the stacked structure;
   b) providing a particulate ceramic insulating material between adjacent layers of the stacked structure;
   c) heating the stacked structure to a temperature sufficient to recrystallise the particulate ceramic insulating material; and
   d) applying pressure to the stacked structure during said heating, wherein the pressure is applied in a direction perpendicular to the plane of the stacked structure, thereby promoting bonding of the stacked structure to provide the hermetically sealed feedthrough.

2. The method of claim 1 comprising:
   e) excavating at least one channel through the planar ceramic insulating wall; and
   f) introducing a conductive material into the at least one channel to provide the at least one conductive channel between the hermetic chamber and the planar conductor.

3. The method of claim 2 comprising:
   g) excavating at least one passage through the planar ceramic insulator; and
   h) introducing a conductive material into the at least one passage to provide at least one conductive passage between an exterior of the hermetic chamber and the planar conductor.

4. The method of claim 3 wherein the at least one passage is offset from the at least one channel such that the passage and channel are not co-linear.

5. The method of claim 1 wherein the step of assembling the stacked structure comprises assembling multiple layers of interleaved planar ceramic insulators and planar metallic conductors.

6. The method of claim 2 wherein the planar conductor comprises a metallic foil having a pattern comprising a plurality of individual conductors isolated from one another in at least one region of the planar conductor and said excavating step comprises excavating the at least one channel through the planar ceramic insulating wall to a corresponding individual conductor.

7. The method of claim 3 wherein the planar conductor comprises a metallic foil having a pattern comprising a plurality of individual conductors isolated from one another in at least one region of the planar conductor and said passage excavating step comprises excavating the at least one passage through the planar ceramic insulator to a corresponding individual conductor.

8. The method of claim 6 wherein the pattern of the metallic foil comprises at least one narrow conductive path that is narrower than other ones of the individual conductors, the method comprising:
   passing an electrical current through the at least one narrow conductive path to cause a discontinuity in the narrow conductive path.

9. The method of claim 6 comprising forming the pattern in the metallic foil using laser machining.

10. The method of claim 1 comprising sintering the planar insulating wall and the planar ceramic insulator prior to said assembling step.

11. The method of claim 1 wherein the assembled planar insulating wall and the planar ceramic insulator comprise at least in part a slurry of a particulate suspended in a liquid.

12. The method of claim 1 wherein the step of applying pressure to the stacked structure comprises applying pressure between 2 and 10 MPa.

13. The method of claim 1 wherein the step of applying pressure to the stacked structure comprises applying pressure of about 2 MPa.

14. The method of claim 1, further comprising:
   providing at least one intermediate planar ceramic insulator including a second conductive channel therethrough, the second conductive channel being non co-linear with the first conductive channel; and
   providing at least one additional planar conductor in conductive communication with the planar conductor via the second conductive channel;
and wherein the plurality of layers of the stacked structure includes the at least one intermediate planar ceramic insulator and the at least one additional planar conductor so that the feedthrough includes the first conductive channel, the planar conductor, the second conductive channel, and the additional planar conductor.

15. The method of claim 1 wherein the planar conductor is in conductive communication with the hermetic chamber via more than twenty five conductive channels through the planar ceramic insulating wall.

16. A method for forming an hermetically sealed feedthrough through an insulating body of an hermetic chamber, the insulating body including a planar ceramic insulating wall, the method comprising:
- a) assembling a stacked structure including a plurality of planar layers, the plurality of layers comprising:
  - the planar ceramic insulating wall defining a plane for the stacked structure;
  - a planar conductor positioned parallel to the plane of the stacked structure, wherein in end use the planar conductor is in conductive communication with the hermetic chamber via at least one conductive channel through the planar ceramic insulating wall;
  - a planar ceramic insulator positioned parallel to the plane of the stacked structure;
- b) providing a particulate ceramic insulating material between adjacent layers of the stacked structure;
- c) heating the stacked structure to a temperature sufficient to recrystallise the particulate ceramic insulating material; and
- d) applying pressure to the stacked structure during said heating, wherein the pressure is applied to provide isostatic pressure within the stacked structure during heating, thereby promoting bonding of the stacked structure to provide the hermetically sealed feedthrough.

\* \* \* \* \*